United States Patent [19]

Stavrianopoulos et al.

[11] Patent Number: 4,987,065

[45] Date of Patent: Jan. 22, 1991

[54] IN VIVO LABELLING OF POLYNUCLEOTIDE SEQUENCES

[75] Inventors: Jannis Stavrianopoulos, New York, N.Y.; Heuy-Lang Yang, Tenafly, N.J.; Norman E. Kelker, New York, N.Y.

[73] Assignee: Enzo Biochem, Inc., New York, N.Y.

[21] Appl. No.: 803,532

[22] Filed: Dec. 2, 1985

Related U.S. Application Data

[63] Continuation of Ser. No. 510,975, Jul. 5, 1983, abandoned.

[51] Int. Cl.$^5$ .................... C12Q 1/70; C12Q 1/68
[52] U.S. Cl. ............................ 435/5; 435/6; 435/91; 435/172.3; 435/252.8; 435/320.1; 935/31; 935/58; 935/72; 935/73; 935/77; 935/78
[58] Field of Search ................ 435/5, 6, 91, 7, 172.3, 435/253, 320, 235; 935/31, 58, 72, 73, 77, 78

[56] References Cited

U.S. PATENT DOCUMENTS 4,358,535 11/1982 Falkow et al. .................... 435/6
4,581,333 4/1986 Kourilsky et al. ................ 435/7 X

OTHER PUBLICATIONS

Shub, D. et al., Abstracts of the Annual Meeting of American Society for Microbiologists, Abstract H3, Mar., 1981.
Casna, N. et al., Gene, vol. 18, pp. 297–307, Sep., 1982.
Huang, L. et al., Nuc. Acids Research, vol. 10, pp. 1579–1591, Mar., 1982.
Birge, E. A. Bacterial and Bacteriophage Genetics, pp. 99–104, Springer-Verlag, New York, 1981.
Warren, R. Ann. Rev. Microbiol., vol. 34, pp. 137–158, 1980.

Primary Examiner—Richard A. Schwartz
Assistant Examiner—Nancy Treptow
Attorney, Agent, or Firm—Serle I. Mosoff; Ronald C. Fedus

[57] ABSTRACT

In vivo labelled polynucleotides, processes for in vivo labelling of polynucleotides, and detection methods and kits characterized by those labelled polynucleotides. The in vivo on biologically-labelled polynucleotides of this invention are useful in the detection of various analytes and in other laboratory, industrial and medical applications.

25 Claims, 1 Drawing Sheet

IN VIVO LABELLING OF POLYNUCLEOTIDE SEQUENCES

This is a continuation of application Ser. No. 510,975, filed July 5, 1983, now abandoned, entitled IN VIVO LABELLING OF POLYNUCLEOTIDE SEQUENCES.

TECHNICAL FIELD OF INVENTION

This invention relates to in vivo labelling of polynucleotide sequences. More specifically, it relates to the biological labelling of DNA sequences that allows their detection upon hybridization to analytes. As will be appreciated, the biologically-labelled polynucleotide sequences produced in accordance with the methods of this invention are useful in many laboratory, industrial and medical applications wherein detection of analytes is desired.

BACKGROUND ART

In the description, the following terms are employed:

Analyte—A substance or substances, either alone or in admixtures, whose presence is to be detected and, if desired, quantitated. The analyte may be a DNA or RNA molecule of small or high molecular weight, a molecular complex including those molecules, or a biological system containing nucleic acids, such as a virus, a cell, or group of cells. Among the common analytes are nucleic acids (DNA and RNA) or segments thereof, either single- or double-stranded, viruses, bacteria, cells in culture, and the like. Bacteria, either whole or fragments thereof, including both gram positive and gram negative bacteria, fungi, algae, and other microorganisms are also analytes, as well as animal (e.g., mammalian) and plant cells and tissues.

Probe—A labelled polynucleotide sequence which is complementary to a polynucleotide sequence of a particular analyte and which hybridizes to said analyte polynucleotide sequence.

Label—That moiety attached to a polynucleotide sequence, which as is, which after covalent attachment to it of a signalling moiety or a combination of bridging moiety and signalling moiety or which after non-covalent binding to it of a signalling moiety or a combination of bridging moiety and signalling moiety, gives rise to a signal which is detectable, and in some cases quantifiable. Compounds carrying such labels include, for example, glucosylated nucleotides, glycosylated nucleotides, 5-hydroxymethyluracil, BrdUR, and 5-methylcytosine.

Bridging Moiety—That moiety which on covalent attachment or non-covalent binding to the label of a polynucleotide sequence acts as a link or a bridge between that label and a signalling moiety.

Signalling Moiety—That moiety which on covalent attachment or non-covalent binding to the label of a polynucleotide sequence or to a bridging moiety attached or bound to that label provides a signal for detection of the label.

Signal—That characteristic of a label or signalling moiety that permits it to be detected from sequences that do not carry the signal.

The analysis and detection of minute quantities of substances in biological and non-biological samples has become a routine practice in clinical and analytical laboratories. These detection techniques can be divided into two major classes: (1) those based on ligand-receptor interactions (e.g., immunoassay-based techniques), and (2) those based on nucleic acid hybridization (polynucleotide sequence-based techniques).

Immunoassay-based techniques are characterized by a sequence of steps comprising the non-covalent binding of an antibody and antigen complementary to it. See for example, T. Chard, *An Introduction To Radioimmunoassay And Related Techniques* (1978).

Polynucleotide sequence-based detection techniques are characterized by a sequence of steps comprising the non-covalent binding of a labelled polynucleotide sequence or probe to a complementary sequence of the analyte under hybridization conditions in accordance with the Watson-Crick base pairing of adenine (A) and thymidine (T), and guanine (G) and cytidine (C), and the detection of that hybridization. [M. Grunstein and D. S. Hogness, "Colony Hybridization: A Method For The Isolation Of Cloned DNAs That Contain A Specific Gene", *Proc. Natl. Acad. Sci. USA*, 72, pp. 3961–65 (1975)].

In a generalized sense, the non-covalent binding of a labelled sequence or probe to a complementary sequence of an analyte is the primary recognition event of polynucleotide sequence-based detection techniques. This binding event is brought about by a precise molecular alignment and interaction of complementary nucleotides of the probe and analyte. It is energetically favored by the release of non-covalent bonding free energy, e.g., hydrogen bonding, stacking free energy and the like.

In addition to the primary recognition event, it is also necessary to detect when binding takes place between the labelled polynucleotide sequence and the complementary sequence of the analyte. This detection is effected through a signalling step or event. A signalling step or event allows detection in some quantitative or qualitative manner, e.g., a human or instrument detection system, of the occurrence of the primary recognition event.

The primary recognition event and the signalling event of polynucleotide sequence based detection techniques may be coupled either directly or indirectly, proportionately or inversely proportionately. Thus, in such systems as nucleic acid hybridizations with sufficient quantities of radiolabeled probes, the amount of radio-activity is usually directly proportional to the amount of analyte present. Inversely proportional techniques include, for example, competitive immunoassays, wherein the amount of detected signal decreases with the greater amount of analyte that is present in the sample.

Amplification techniques are also employed for enhancing detection wherein the signalling event is related to the primary recognition event in a ratio greater than 1:1. For example, the signalling component of the assay may be present in a ratio of 10:1 to each recognition component, thereby providing a 10-fold increase in sensitivity.

A wide variety of signalling events may be employed to detect the occurrence of the primary recognition event. The signalling event chosen depends on the particular signal that characterizes the label or signalling moiety of the polynucleotide sequence employed in the primary recognition event. Although the label itself, without further treatment to attach or to bind to it a signalling moiety or a combination of bridging moiety and signalling moiety, may be detectable, it is more usual either to attach covalently or to bind non-covalently to the label a signalling moiety or a combination of bridging moiety and signalling moiety that is itself detectable or that becomes detectable after further modification.

It should, of course, be understood that the combination of bridging moiety and signalling moiety, described above, may be constructed before attachment or binding to the label, or it may be sequentially attached or bound to the label. For example, the bridging moiety may be first bound or attached to the label and then the signalling moiety combined with that bridging moiety. In addition, it should be understood that several bridging moieties and/or signalling moieties may be employed together in any one combination of bridging moiety and signalling moiety.

Examples of the covalent attachment of a signalling moiety or a combination of bridging moiety and signalling moiety to a label are the chemical modification of the label with signalling moieties, such as radioactive moieties, fluorescent moieties or other moieties that themselves provide signals to available detection means or the chemical modification of the label with at least one combination of bridging moiety and signalling moiety to provide that signal.

Examples of the non-covalent binding of a signalling moiety or a combination of bridging moiety and signalling moiety to a label are the non-covalent binding to the label of a signalling moiety that itself can be detected by appropriate means, or the non-covalent binding to the label of a combination of bridging moiety and signalling moiety to provide a signal that may be detected by one of those means. For example, the label of the polynucleotide sequence may be non-covalently bound to an antibody, a fluorescent moiety or another moiety which is detectable by appropriate means. Alternatively, the label could be bound to a bridging moiety, e.g., a lectin, and then bound through the lectin, or bridging moiety, to another moiety that is detectable by appropriate means.

There are a wide variety of signalling moieties and bridging moieties that may be employed for covalent attachment or non-covalent binding to the labels of polynucleotide sequences useful as probes in analyte detection systems. They include both a wide variety of radioactive and non-radioactive signalling moieties and a wide variety of non-radioactive bridging moieties. All that is required is that the signalling moiety provide a signal that may be detected by appropriate means and that the bridging moiety, if any, be characterized by the ability to attach covalently or to bind non-covalently to the label and also the ability to combine with a signalling moiety.

Radioactive signalling moieties and combinations of various bridging moieties and radioactive signalling moieties are characterized by one or more radioisotopes such as $^{32}P$, $^{131}I$, $^{14}C$, $^{3}H$, $^{60}Co$, $^{59}Ni$, $^{63}Ni$ and the like. Preferably, the isotope employed emits $\beta$ or $\gamma$ radiation and has a long half life. Detection of the radioactive signal is then, most usually, accomplished by means of a radioactivity detector, such as exposure to a film.

Non-radioactive signalling moieties and combinations of bridging moieties and non-radioactive signalling moieties are being increasingly used both in research and clinical settings. Because these signalling and bridging moieties do not involve radioactivity, the techniques and labelled probes using them are safer, cleaner, generally more stable when stored, and consequently cheaper to use. Detection sensitivities of the non-radioactive signalling moieties also are as high or higher than radiolabelling techniques.

Among the preferred non-radioactive signalling moieties or combinations of bridging - signalling moieties useful with non-radioactive labels are those based on the biotin/avidin binding system. [P. R. Langer et al., "Enzymatic Synthesis of Biotin-Labeled Polynucleotides: Novel Nucleic Acid Affinity Probes", Proc. Natl. Acad. Sci. USA, 78, pp. 6633-37 (1981); J. Stavrianopoulos et al., "Glycosylated DNA Probes For Hybridization/Detection of Homologous Sequences", presented at the Third Annual Congress For Recombinant DNA Research (1983); R. H. Singer and D. C. Ward, "Actin Gene Expression Visualized In Chicken Muscle Tissue Culture By Using In Situ Hybridization With A Biotinated Nucleotide Analog", Proc. Natl. Acad. Sci. USA, 79, pp. 7331-35 (1982)]. For a review of non-radioactive signalling and bridging-signalling systems, both biotin/avidin and otherwise, see D. C. Ward et al., "Modified Nucleotides And Methods Of Preparing And Using Same", European patent application No. 63879.

Non-radioactively labelled polynucleotides are not more widely used in detection systems because the attachment of a label, whch does not interfere with hybridization, to the polynucleotide sequences that are useful as probes in those detection systems is expensive.

First, the chemical reaction conditions that might be useful for modification of a polynucleotide polymer to add to it a label are often too vigorous to be sufficiently selective for a particular nucleotide. More importantly, chemical labelling of polynucleotide sequences often interferes with hybridization because the label interferes with the hydrogen bonding necessary for hybridization. For example, dicarbonyl reagents, such as kethoxal or glyoxal, react with guanine residues [Shapiro et al., Biochemistry, 5, pp. 2799-2807 (1966); M. Litt, Biochemistry, 8, pp. 3249-53 (1969); Politz et al., Biochemistry, 20, pp. 372-78 (1981)]. However, the kethoxal and glyoxal labelled nucleotides do not hybridize to complementary sequences in the analyte because the label interferes with the hydrogen bonding necessary for hybridization.

Accordingly, in order to label a polynucleotide sequence for use as a probe, a labelled monomeric nucleotide must be synthesized and then incorporated into a polynucleotide sequence. Various methods are available to label an individual nucleotide in such a way that the label does not interfere with hybridization. Various methods, both chemical and enzymatic, are also available to attach those labelled monomeric nucleotides to a polynucleotide probe. For example, a labelled nucleotide, such as 2'-deoxyuridine 5'-triphosphate 5-allylamine biotin may be substituted in DNA probes by nick translation [P. R. Langer et al., "Enzymatic Synthesis Of Biotin-Labeled Polynucleotides: Novel Nucleic Acid Affinity Probes", Proc. Natl. Acad. Sci. USA, 78, pp. 6633-37 (1981)] or by terminal addition to DNA probes using terminal deoxynucleotidyl transferase.

There are, however, production limitations with these processes. For example, it is necessary to synthesize the labelled monomeric nucleotides prior to incorporating them into the polynucleotide probes. This synthesis may sometimes involve expensive chemical processes. The coupling of the labelled monomeric nucleotides into a polynucleotide is also expensive. For example, the enzymes employed in enzymatic coupling are costly. Related limitations include the difficulties and cost in scale-up of such processes to commercial levels. As a result, these processes currently produce non-radioactively labelled polynucleotides that are more costly than are desired.

DISCLOSURE OF THE INVENTION

The present invention solves the production limitations referred to above by providing in vivo or biologically labelled polynucleotide sequences that are useful as probes in detection of analytes. These sequences may be utilized in methods and kits for detecting analytes of interest.

The processes for preparaing the labelled DNA sequences of this invention generally involve, in one embodiment, the in vivo labelling of desired polynucleotide sequences. Alternatively, the processes of this invention may be employed to incorporate in vivo into a desired polynucleotide sequence a previously labelled base, nucleoside or nucleotide. Both embodiments of this invention are improvements over prior processes for labelling polynucleotides. Both make non-radioactively-labelled probes more readily available at less cost for use in various detection systems.

More specifically, the first embodiment of the process for in vivo labelling of polynucleotide sequences of this invention comprises the step of culturing a host characterized by a polynucleotide sequence that is desired to be labelled and at least another polynucleotide sequence that expresses a product that labels the desired polynucleotide sequence on its replication in the cultured host. Preferably, the method also includes the step of isolating from the cultured host at least a polynucleotide sequence comprising the labelled polynucleotide sequence. More preferably, the DNA sequence isolated from the cultured host is part or all of the labelled polynucleotide sequence itself.

In one preferred embodiment of this invention a heterologous DNA sequence that is desired to be labelled is inserted into the T4 bacteriophage genome (which normally contains hydroxymethylated and glucosylated DNA). The host T4 phage is grown under conditions wherein it produces hydroxymethylated and glucosylated DNA. The T4 phage containing the inserted probe DNA sequence is harvested, and the probe DNA sequence is preferably excised for use as a hybridization probe in any of the well-known in situ or in vitro hybridization procedures (e.g., Southern blot, Northern blot, dot blot, colony hybridization or plaque lift). Alternatively, the entire T4 phage genome containing the inserted, in vivo labelled probe DNA sequence may be used as the probe.

The presence of the probe hybridized to the analyte is then detected, for example, by using a combination of bridging moiety and signalling moiety. For example, Concanavalin A ("Con A") is bound to the glucosylated probe DNA sequence and there acts as a bridge to a naturally glycosylated enzyme. The enzyme, e.g., horseradish peroxidase, upon contact to the proper substrate, e.g., $H_2O_2$ and diaminobenzidine, produces colorimetric products which can be detected. In addition, other lectin detection systems or antibody or other detection systems utilizing well-known processes may also be used to detect the hybridized DNA sequence.

In another embodiment of the process of this invention, a base, nucleoside or nucleotide, or analogue or precursor thereof, that carries the desired label, is incorporated in vivo into a polynucleotide sequence. In this embodiment the process for in vivo labelling of polynucleotide sequences of this invention comprises the step of culturing a host characterized by the polynucleotide sequence that is desired to be labelled in the presence of a base, nucleoside or nucleotide, or analogue or precursor thereof, that carries the label, the host requiring the base, nucleoside or nucleotide for its growth, thereby incorporating the label into the polynucleotide sequence. Again, it is preferable to isolate from the cultured host at least a polynucleotide sequence comprising the labelled polynucleotide sequence. More preferably, the sequence isolated from the cultured host is part or all of the labelled polynucleotide sequence itself.

In one preferred embodiment of this process for in vivo incorporation of a base, nucleoside or nucleotide, or analogue or precursor thereof, that carries a label, into a polynucleotide sequence, a thymine or thymidine requiring mutant of E. coli characterized by the polynucleotide sequence that is desired to be labelled, is grown on a medium supplemented with BrdUR in place of thymidine or thymine to label biologically the desired polynucleotide sequence with BrdUR.

Subsequent use of this labelled probe is essentially as set forth above. Detection of the probe/analyte hybridization event may be effectuated through the biotinylation of the BrdUR labelled probe DNA sequence and subsequent detection of the biotin moieties by any of several known methods. Alternatively, antibody or other detection systems may also be used to detect BrdUR-substituted DNA directly. [H. G. Gratzner, "Monoclonal Antibody To 5-Bromo-and 5-Iodo-deoxyuridine: A New Reagent For Detection Of DNA Replication", Science, 218, pp. 474–75 (1982)].

BEST MODE OF CARRYING OUT THE INVENTION

Figure 1:
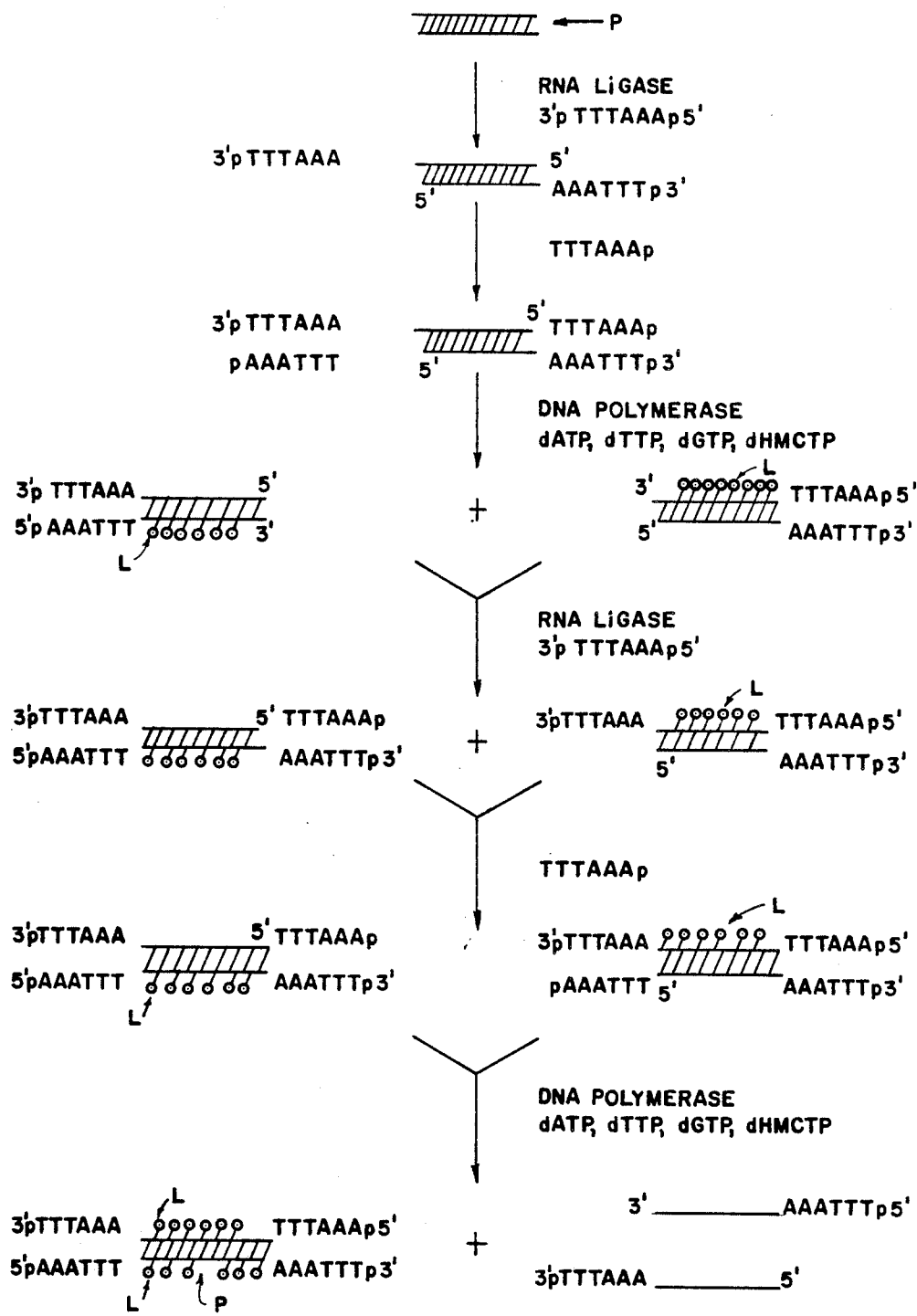
FIG. 1 is a schematic outline of one embodiment of a process for attaching an AhaIII restriction endonuclease site to both ends of a probe DNA sequence for use in the in vivo labelling process of this invention.

In order that the invention herein described may be more fully understood, the following detailed description is set forth.

SOURCES OF IN VIVO LABELLED POLYNUCLEOTIDES

Any of a large number of polynucleotide sequences may be employed in the processes of this invention to be labelled and to be used in the detection of analytes. Included, for example, are polynucleotide sequences that characterize various viral, viroid, fungal, parasitic or bacterial infections, genetic disorders or other sequences in analytes that it is desired to detect. They may be of synthetic, semi-synthetic or natural origin.

Any of a large number of available sources may be used to produce in vivo labelled polynucleotides. Included are, for example, the T-even phages (i.e., T2, T4, and T6), which naturally substitute glucosylated hydroxymethyldeoxycytidine monophosphate for cytidine monophosphate [I. R. Lehman et al., J. Biol. Chem., 235, pp. 3254–59 (1960)]; the Bacillus subtilis phage SPO1, which replaces thymidine residues with 5-hydroxymethyluracil [R. G. Kallen et al., J. Mol. Biol., 5, pp. 248–50 (1962)]; the Xanthomonus oryzae phage XP12, which replaces C residues with 5-methylcytosine [T. T. Kuo et al., J. Mol. Biol., 34, pp. 373–75 (1968)]; the Bacillus subtilis phage SP15, wherein 62 percent of the T residues are replaced by phosphoglucuronated and glucosylated 5-(4',5'-dihydroxypentyl) uracil [H. Hayashi et al., *J. Amer. Chem. Soc.*, 95, pp. 8749-57 (1973)]; and in a variation of the invention, labelling of probe DNA sequences with 5-bromodeoxyuridine (BrdUR) or other labelled bases, nucleosides or nucleotides by growing mutants requiring those bases, nucleosides or nucleotides for growth in the presence of them.

The polynucleotide sequence that is desired to be labelled and the source of the label may be combined in the host in a large variety of ways. For example, the polynucleotide sequence to be labelled may be originally part of the native genome of a particular host or it may be inserted into that genome using, for example, the methodology of recombinant DNA technology. Alternatively, the polynucleotide sequence to be labelled may be part of a cloning vehicle, phage DNA or other DNA sequence used to transfect a host for replication therein and labelling.

The source of the label may also be present in the host in a variety of ways. For example, when the source of the label is a DNA sequence that expresses a product that labels the desired polynucleotide sequence on its replication in a host characterized by that polynucleotide sequence, that DNA sequence may be present in the host because it was originally part of the natural genome of the host or because it was inserted into that genome. Alternatively, the DNA sequence that is the source of the label may be part of a cloning vehicle, phage DNA or other DNA sequence used to transfect the host for replication therein. In one preferred embodiment of this invention, the polynucleotide sequence to be labelled is present in the same cloning vehicle or phage DNA as the DNA sequence that is the source of the label. Alternatively, the two DNA sequences may be separately present in the host. Most preferably, the polynucleotide sequence to be labelled is cloned into the DNA sequence that is the source of the label. In any event, on culturing the host the desired DNA sequence is labelled during or after replication as a result of the product expressed by the DNA sequence that is the source of the label.

When the source of the label is a base, nucleoside or nucleotide, or analogue or precursor thereof, that is incorporated into the desired polynucleotide sequence on replication in a host because the host is a variant which requires that label carrying moiety for growth, the base, nucleoside or nucleotide or an analogue or a precursor thereof, that carries the desired label, is added to the culture medium. Then, on culturing in accordance with the processes of this invention, the desired polynucleotide sequence is labelled in vivo on its replication in the host by incorporation of the label.

Hosts useful in the processes of this invention may be selected from a wide variety of known organisms. They include, for example, various microorganisms, such as *E. coli*, Bacillus, Pseudomonas, Streptomyces, as well as a variety of fungi, algae, and plant and human cells in culture. It is only necessary that the polynucleotide sequence that is desired to be labelled will replicate in the host and that it will be labelled by the source of the label under the culture conditions selected for growth of the host.

SOURCES AND DETECTION OF ANALYTES

The biologically-produced probe DNA sequences of this invention have many practical uses. One use is in the detection of analytes. The analyte to be detected can be present in any biological or non-biological sample, such as clinical samples, for example, blood, urine, feces, saliva, pus, semen, serum, other tissues, fermentation broths, culture media, and the like.

If necessary, the analyte may be pre-extracted or purified by known methods to concentrate its nucleic acids. Such nucleic acid concentration procedures include, for example, phenol extraction, treatment with chloroform-isoamyl alcohol or chloroform-octanol, column chromatography (e.g., Sephadex, hydroxyl apatite), and CsCl equilibrium centrifugation. The analyte, together with contaminating materials, if present, may be tested in the mixture, as purified, or the analyte may be immobilized before analysis.

There are also many applications for the detection methods and kits of this invention. Any analyte desired to be detected and analyzed in any sample can be subject to the methods and kits of the invention. For example, the methods and kits may be employed to detect and to identify viral and bacterial DNA sequences, e.g., the detection of herpes virus.

The methods and kits of this invention can also be utilized to diagnose human genetic disorders by preparing a probe complementary to a DNA sequence which is associated with the genetic disorder and detecting the presence or absence of any primary recognition events. Among these genetic disorders, for example, is thalassemia. The diagnosis of thalassemia can be made by hybridization of probe polynucleotide sequences to genomic DNA.

Another use for the methods and kits of this invention is in chromosomal karyotyping, which comprises using a series of labelled polynucleotide sequences, corresponding to a series of defined DNA sequences uniquely located on each of the chromosomes, and then detecting primary recognition events thereon.

METHODS OF HYBRIDIZATION ANALYSIS

For testing, the composition suspected of containing the analyte is incubated with the labelled probe polynucleotide sequence for a time and under conditions sufficient to allow hybridization between the polynucleotide sequence of the analyte and the recognizing polynucleotide sequence on the probe. These conditions will vary depending on the nature and amount of the analyte and of the probe [D. E. Kennell, "Principles And Practices Of Nucleic Acid Hybridization", *Progr. Nucl. Acid Res. Mol. Biol.*, 11, pp. 259-301 (1971)].

A wide variety of signalling events may be employed to detect the occurence of the primary recognition event — the hybridization of the labelled DNA sequence to a complementary sequence in the analyte. The particular signalling event chosen depends on the particular signal that characterizes the label or modified label of the polynucleotide sequence.

For example, the label carried by the polynucleotide sequence may, without further treatment to attach or to bind to it a signalling moiety or at least one combination of bridging moiety and signalling moiety, be detectable. However, it is more usual, either to attach covalently or to bind noncovalently to the label a signalling moiety, or at least one combination of bridging moiety and signalling moiety that is itself detectable or that becomes detectable after further modification [supra].

Examples of signalling and bridging moieties that may be covalently attached to the labels of polynucleotide sequences include radioactive compounds, fluorescent compounds, fluorescein, rhodamine, dansyl, magnetic compounds, chelating agents and other signalling and bridging moieties which may be covalently attached to those labels.

Examples of signalling and bridging moieties that may be non-covalently bound to the labels of polynucleotide sequences include polypeptides, proteins, lectins, Concanavalin A, enzymes, alkaline phosphatases, acid phosphatases, antigens, antibodies, polypeptides having streptavidin groups attached thereto, $\beta$-galactosidase, glucose oxidase, horseradish peroxidase, chelating agents and other signalling and bridging moieties that may be non-covalently bound to those labels.

For example, an enzyme might be noncovalently bound as a signalling moiety to the label on the polynucleotide probe sequence. Then substrate would be added to obtain color development (fluorescence, radioactivity or chelation detection systems may also be used). Alternatively, if the moiety bound to the label were a biotin moiety, for example, then a biotin binding molecule such as avidin, streptavidin or anti-biotin antibody, would then be added thereto. The biotin binding molecule would then be conjugated to an enzyme, a fluorescent compound, an electron dense compound, or an insoluble solid phase, and detection carried out by appropriate means.

In order that this invention may be better understood, the following examples are set forth. These examples are for purposes of illustration only and this invention should not be considered to be limited by any recitation used therein.

EXAMPLE I (A) Production of Glucosylated Probe DNA in Bacteriophage T4

Using the techniques of recombinant DNA technology, a probe DNA sequence can be inserted into a T4 bacteriophage for labelling with glucosyl residues.

T4 DNA is naturally glucosylated. Because most of the commonly used restriction endonucleases do not hydrolyze glucosylated DNA, it may be necessary to remove the glucose residues from the T4 DNA prior to endonucleolytic cleavage and insertion of the probe DNA. Hydroxymethyl cytidine glucosylase, a phage induced enzyme, removes glucose moieties from glucosylated DNA and transfers them to UDP in its reverse reaction [J. Josse et al., *J. Biol. Chem.*, 237, pp. 1968–76 (1962); S. R. Zimmerman et al., *J. Biol. Chem.*, 237, pp. 512–18 (1962)]. Alternatively, T4 phages may be grown under conditions in which cytosine replaces the hydroxymethyl derivatives. [K. Carlson et al., *J. Virol.*, 36, pp. 1–17 (1979); P. O'Farrell et al., *Mol. Gen. Genet.*, 179, pp. 421–35 (1980); L. Snyder et al., *Proc. Natl. Acad. Sci. USA*, 73, pp. 3098–3102 (1976)].

Once the T4 DNA has been deglucosylated as set forth above, the probe DNA sequence is inserted into the deglucosylated T4 genome. Although insertion of the probe DNA sequence into the deglucosylated T4 genome may be effected in a variety of known ways, it is preferable to insert it in such a manner that it may be removed from the T4 DNA subsequent to labelling.

Because in T4 phages only the C residues are glucosylated, the restriction endonuclease Aha III, which recognizes and cleaves the DNA sequence TTTAAA, is one of the few endonucleases which can cleave native T4 DNA. Accordingly, in one preferred embodiment of this invention, the probe DNA sequence is modified so that it carries an AhaIII restriction site at both ends before insertion into the partially deglucosylated T4 DNA (FIG. 1). In such a construction, the probe DNA sequence may then be isolated after labelling from the T4 DNA by restriction with AhaIII.

A general protocol for the preparation and insertion of a DNA probe into T4 DNA and its removal after labelling is described below and illustrated in FIG. 1:

(1) The DNA sequence pTTTAAAp (synthesized by known techniques) is first attached to the 3' ends of the probe DNA (P) which is to be inserted within the T4 genome utilizing RNA ligase. The phosphates are necessary at both the 3' and 5' ends of the DNA sequence pTTTAAAp to prevent the formation of concatemers.

Primer DNA sequence TTTAAAp (synthesized by conventional methods) is then non-covalently bound to the above-produced DNA sequence (FIG. 1). This DNA sequence (TTTAAAp) serves as a primer so that on replication in the presence of DNA polymerase and the deoxynucleotide triphosphates dATP, dTTP, dGTP and deoxyhydroxymethyl CTP (dHMCTP) two DNA sequences are produced (FIG. 1). These sequences carry the AhaIII restriction endonuclease site at opposite ends of the probe DNA sequence (FIG. 1). They also carry a label (L) ( ) on one of the DNA strands.

In order to add a second AhaIII site to the other end of the probe DNA sequence a similar series of steps is performed. Again, the DNA sequence pTTTAAAp is attached to the 3' ends of the previously produced DNA sequences (FIG. 1). Then, the DNA sequence TTTAAAp is again employed as a primer to bind non-covalently to the produced sequences (FIG. 1) and the primed sequences replicated in the presence of DNA polymerase and the four deoxynucleotide triphosphates as before (FIG. 1).

As a result of this series of steps a DNA sequence, comprising the probe DNA sequence flanked at each end by an AhaIII restriction endonuclease site and carrying a label on both DNA strands, is produced (FIG. 1). As a by-product of these steps two single-stranded DNA sequences are also produced. These single-stranded DNA sequences may be easily separated from the desired probe DNA sequence carrying the two AhaIII restriction sites.

Phosphate groups are then removed from the ends of the probe DNA sequence with alkaline phosphatase prior to insertion of the probe DNA sequence into the T4 genome.

(2) Partially deglucosylated phage T4 DNA, produced as set forth above, is cleaved with restriction endonucleases preparatory to insertion of the probe DNA into a nonessential portion of the T4 genome, i.e., those genes not necessary for phage replication, hydroxymethyl cytosine production and DNA glucosylation. BamHI cleaves T4 DNA at such a site. After restriction, if necessary, the single-stranded tails are filled in by DNA polymerase I in the presence of ATP, TTP, GTP and deoxyhydroxymethyl CTP.

(3) The probe DNA sequence, tailed with the AhaIII recognition sites, is blunt end ligated into the previously restricted nonessential region of the T4 genome [V. Sgaramella, "Enzymatic Oligomerization of Bacteriophage P22 DNA And Of Linear Simian Virus 40 DNA", *Proc. Natl. Acad. Sci. USA*, 69 pp. 3389–93 (1972)].

(4) After the probe is inserted into the T4 genome, the entire recombinant DNA molecule is preferably glucosylated with the $\alpha$ and $\beta$ glucosyl transferases in the presence of UDP-glucose [J. Josse et al., supra] in vitro to protect the recombinant DNA molecule from phage endonucleolytic attack.

(5) In vitro encapsulation of the recombinant T4 probe DNA molecule may be done according to the procedure of L. W. Black, "In Vitro Packaging Of Bacteriophage T4 DNA", *Virology*, 113, pp. 336–44 (1981).

(6) Screening of the transformed host T4 phages for those clones containing probe DNA sequences is done by hybridization with complementary biotinylated DNA probes, or with any other conventional screening method.

(7) DNA is isolated from T4 clones containing the probe DNA by any of the many known methods [see, for example, G. L. Cantoni and D. R. Davies (Eds.), *Procedures in Nucleic Acid Research*, New York: Harper and Row (1966)].

(8) The in vivo labelled probe DNA sequences may be excised from the recombinant T4 genome for subsequent use in detection systems by cleaving with the AhaIII restriction endonuclease at the flanking sequences produced as set forth above. Alternatively, the entire recombinant T4 genome containing the probe DNA sequence may be utilized as the probe.

B. Detection of Glucosylated DNA sequences: Use of Concanavalin A - Glycosylated Enzyme Complexes Con A, a bridging moiety, binds to both glucosylated DNA and to glycosylated proteins (a signalling moiety). At pH 5 and temperatures below room temperature, Con A is a dimer having two glycosyl-binding sites. At physiological pH and room temperature, or slightly above (37° C.), native Con A is a tetramer and contains four binding sites. At alkaline pH (8.5 and above) and higher temperatures, Con A dissociates into inactive subunits. Manganese or magnesium and calcium are required for Con A to bind glycosyl residues. Stock solutions of Con A are kept in glass tubes at a concentration of 1–5 mg/ml in TCMN buffer (5 mM Tris HCl, pH 7.0, 1 mM $CaCl_2$, 1 mM $Cl_2$, 1M NaCl) because Con A adheres to plastic surfaces and aggregates at concentrations greater than 5 mg/ml. Con A can be stored at 4° C. for about 3 months.

(1) Sequential Treatment of Glucosylated DNA Sequences with Con A and Glycosylated Enzyme Nitrocellulose paper containing glucosylated T4 DNA dots was blocked overnight at 42° C. in a humidity chamber in a buffer containing 2% acidified bovine serum albumin (BSA), 1 X TCMN and 0.1% V/V Triton X-100. The nitrocellulose filters were then rinsed three times, for 5 minutes each time, with a buffer containing 1% BSA and 1 X TCMN. The nitrocellulose filters were then incubated in a Con A solution consisting of 100–200 µg Con A/ml in 0.1% BSA and 1 X TCMN. The solution was applied at 0.018 ml/cm² of nitrocellulose filter or 0.2 ml/cm² of Whatman ® 3 MM paper, and was incubated for 1 h at 37° C. Following incubation, the filters were rinsed 3–4 times, for 5 min each time, in a 0.1% BSA and 1 X TCMN buffer. The filters were incubated in a solution of 0.1% BSA and 1 X TCMN containing 2–10 units of enzyme. The solutions were applied at 0.018 ml/cm² of nitrocellulose and 0.2 ml/cm² of Whatman ® 3 MM filters. Incubation was at 37° C. for 1 h. The filters were then rinsed 3 times, for 5 min each time, in NBTT buffer (0.5M NaCl, 0.1% BSA, 0.05% Tween 20, 10 mM Tris HCl, pH 7.2) and 2 times, for 5 min each time, in NCBT buffer (0.3M NaCl, 0.03M Na citrate, 0.1% BSA, and 0.05% Tween 20).

The glycosylated enzyme-Con A-derivatized DNA sequences were detected as follows:

(A) Horseradish Peroxidase

The filter containing Con A-glucosylated DNA and glycosylated enzyme was soaked in a freshly prepared solution containing 5 mg of diaminobenzidine, 0.01% $H_2O_2$ in 10 ml of 5 mM Tris HCl at pH 7.5 and protected from light. A brown color was produced as indicator.

(B) Acid Phosphatase

The filter containing Con A-glucosylated DNA and glycosylated enzyme was dipped into a substrate solution containing 0.1 mg Naphthol AS-MX phosphoric acid/ml of 0.2M NaOAc at pH 5.8, and incubated at 37° C. in the dark. A rosy red color was produced as indicator.

(C) Glucose Oxidase 6.7 mg of $\beta$-D glucose and 0.67 mg of Nitro Blue Tetrazolium/ml of 50 mM Tris/HCl (pH 7.5) were incubated at 37° C. for 1 h. 100 µl of 100 x PMS (Phenazine methosulfate; 0.0167 mg/ml in distilled $H_2O$) was added and the solutions were mixed. The filter containing Con A-glucosylated DNA and glycosylated enzyme was then incubated in this mixture, in the dark for 1 h at 37° C. or overnight at room temperature. An intense blue color was produced as the indicator.

Sensitivities of the reactions:

(A) Horseradish Peroxidase

150–250 picograms of DNA was detected. Color faded after storage.

(B) Acid Phosphatase

Only hybridized DNA blots were analyzed, 7–15 picograms of DNA were detected.

(C) Glucose Oxidase

Only glucosylated DNA blots were checked, 150–250 picograms of DNA were detected.

This protocol for Con A detection was found to be non-optimal. The sequential addition of Con A followed by enzyme was found to give excessive background in the assay detection system. The procedure was also relatively time consuming and the sensitivity of detection was lower than desired. Therefore a second method of contacting Con A, glucosylated DNA and enzyme was employed.

(2) Treatment of Glucosylated DNA Sequences with Complexed Con A/Glycosylated Enzyme Con A and glycosylated enzyme were mixed in a 1:1 molar ratio in TCMN buffer and incubated at 37° C. for 2 h or at 25° C. for 4–6 h or at 4° C. overnight to 48 h. (At the end of the incubation period the mixture should be clear. If it is not, Con A is present in excess and more enzyme must be added.)

The blocking of nitrocellulose filters containing T4 glucosylated DNA was done as set forth above. The filters were then rinsed 3 times, for 5 min each time, in TCMN buffer and 1% BSA. The Con A-enzyme complex prepared above was then contacted to the filter at a volume of 0.018 ml/cm², or in an amount containing about 2–10 units of enzyme. Incubation was at 37° C. for 1 h. After incubation the filters were first rinsed 3 times, for 5 min each time, in NBTT and then 2 times, for 5 min each time, in NCBT.

The horseradish peroxidase reaction was performed as set forth above. With this procedure it was possible to detect 31.25 picograms of DNA and there was significantly less background than with the previously described detection technique. Similar detection procedures can also be performed utilizing a Con A-acid phosphatase complex, a Con A-glucose oxidase complex, as well as other similiar Con A-enzyme complexes.

Lectin/antibody and other detection systems may also be used [see Ward et al., supra.].

EXAMPLE II

Biotinylation Of Glucosylated T4 DNA

In order to aid in the detection of hybridization reactions between glucosylated probe DNA and analytes, the glucosylated probe DNA may be further derivatized with biotin moieties, for which standard detection systems are known.

One ml of 1 mg/ml T4 DNA in 0.1M sodium acetate buffer (pH 4.3), was mixed with 0.1 ml of a freshly prepared 1M NaIO$_4$ solution. The mixture was incubated for 3 h at room temperature in the dark.

After the oxidation reaction was completed, the solution was dialyzed at 4° C., in the dark, against 2 changes of 0.05M sodium acetate at pH 4.0, 0.1M NaCl and 2 changes of 0.3M sodium borate at pH 9.0–9.3, 0.1M NaCl. The solution was then made 0.4M in 1,6-diaminohexane from a pH 9.3 stock solution of diamine. The mixture was incubated in the dark for 90 min. The resulting Schiff base was reduced with NaBH$_4$. NaBH$_4$, freshly dissolved in water to a concentration of 2M, was added to the mixture at four 30 min intervals, producing incremental concentrations of NaBH$_4$ of 0.025M to 0.1M. Total incubation time was 3 h. The NaBH$_4$ was quenched by adjusting the pH to 5.0–5.5 by adding 4M sodium acetate, pH 4.0. The DNA containing solution was dialyzed 12 h in 0.1M sodium phosphate, pH 6.7, and then made 40% V/V DMF and 20 mM biotin NHS ester. Ths solution was incubated for 12 h. Excess biotin and biotin NHS ester were removed by filtration through a G50 Sephadex column using 1 x SSC as the eluting buffer. Fractions containing DNA were collected from the column, combined, and dialyzed against a solution containing 0.1M NaCl, 0.001M EDTA, pH 7.0, and stored until further use at −20° C.

EXAMPLE III

Production of BrdUR Labelled DNA Sequences in Transformed Thymine Requiring *E. coli* Mutants In this example, a label is incorporated in vivo into a polynucleotide sequence by culturing a host containing the polynucleotide sequence desired to be labelled in the presence of an analogue of a nucleotide, base or nucleoside carrying that label, because the host is a variant which requires the label-carrying analogue. As described previously, the polynucleotide sequence desired to be labelled may be part of the genome of the host or added to the genome. It may also be a part of a DNA sequence or other cloning vehicle or phage employed to transfect the host.

A thymine requiring mutant of *E. coli* (thy A) characterized by a DNA sequence that is desired to be labelled is grown in a medium supplemented with 5-bromodeoxyuridine (BrdUR) in place of thymidine according to the technique of Miller, *Experiments In Molecular Genetics*, Cold Spring Harbor Laboratory (1972). The cells are harvested and a DNA sequence containing the labelled probe DNA sequence is isolated. This DNA sequence can be used directly for hybridization studies. Alternatively, all or part of the labelled probe sequence may first be removed from the remainder of the DNA sequence by endonucleolytic cleavage, and used alone for detection of analytes.

Hybridization of labelled probe to analyte can be detected by reaction with monoclonal or polyclonal antibodies to BrdUR [Gratzner, "Monoclonal Antibody To 5-Bromo- And 5-Iododeoxyuridine: A New Reagent For Detection Of DNA Replication", *Science*, 218, pp. 474–75 (1982)]. Alternatively, the probe can be further chemically derivatized by adding a moiety such as thiobiotin. The thiobiotinized DNA probe can then be detected when hybridized to analytes by the use of biotin detection systems such as Detek® I-hrp, or other such biotin detection systems.

EXAMPLE IV

Biotinylation Of DNA Containing 5-Bromodeoxyuridine

In order to detect BrdUR-labelled probe DNA, as produced in Example III, hybridized to an analyte, BrdUR-labelled probe DNA may be further derivatized with biotin.

Two hundred μg of triethylammonium salt of DNA containing bromodeoxyuridine residues was dissolved in 2 ml of anhydrous dimethylformamide (DMF). To this solution, 0.5 ml of 50 mM thiobiotin in anhydrous DMF was added and the mixture was incubated for 2 h at 60° C. under argon gas. The solvent was removed by evaporation under a reduced pressure at 40° C. The residue was dissolved in 0.5 ml 1 x SSC. Undissolved material was removed by centrifugation. Excess biotin was removed from the supernatant by filtration on a G50 Sephadex column utilizing 1 x SSC as the elution buffer. DNA containing fractions were collected from the column, combined, and stored at −70° C. for future use.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented hereinbefore by way of example.

We claim:

1. A process for in vivo labeling of hybridizable polynucleotide sequences with modified nucleic acid bases, comprising the steps of:
   (a) providing a host, whose genetic information comprises
      (i) a first polynucleotide sequence capable of incorporating at least one modified base upon replication and a second polynucleotide sequence which confers upon said host, a requirement for an exogenous source of a base, or
      (ii) a first polynucleotide sequence having a base capable of being enzymatically modified upon replication, and a second polynucleotide sequence of bacteriophage origin, that is capable of coding for an enzyme that modifies the modifiable base of the first polynucleotide sequence;
   (b) replicating said host under conditions that provide or permit production of such modified base, such that it becomes part of and thereby labels the first polynucleotide sequence, so as to yield a labeled polynucleotide probe; and
   (c) isolating said labeled polynucleotide probe.

2. A process for in vivo labeling of a hybridizable polynucleotide sequence with a modified nucleic acid base, comprising the steps of:
 (a) providing a host whose genetic information comprises a first polynucleotide sequence having a base capable of being enzymatically modified upon replication, and
  a second polynucleotide sequence of bacteriophage origin, that is capable of coding for an enzyme that modifies the modifiable base of the first polynucleotide sequence; and
 (b) replicating said host under conditions that permit production of said modified base such that it becomes part of and thereby labels the first polynucleotide sequence, so as to yield a labeled polynucleotide probe; and
 (c) isolating said labeled polynucleotide probe.

3. A process for in vivo labeling of a hybridizable polynucleotide sequence with modified nucleic acid bases, comprising the steps of:
 (a) providing a host, whose genetic information comprises a first polynucleotide sequence capable of incorporating at least one modified base upon replication and a second polynucleotide sequence which confers a requirement for an exogenous source of said modified base upon said host;
 (b) providing said modified base to said host;
 (c) replicating said host such that said modified base becomes part of and thereby labels the first polynucleotide sequencef; and
 (d) isolating said labeled polynucleotide sequence.

4. A process for labeling and detecting homologous DNA sequences in a biological material which comprises:
 (a) labeling a cloned DNA sequence by inserting said cloned DNA sequence into a suitable bacteriophage which replaces a normal nucleotide of DNA with a naturally-occurring highly modified nucleotide;
 (b) infecting a sensitive bacterial host with said bacteriophage under conditions which allow replication of the bacteriophage DNA with the highly modified nucleotide, and isolating the labeled bacteriophage DNA;
 (c) hybridizing said DNA having a naturally-occurring highly modified nucleotide with said biological material; and
 (d) detecting said hybridized DNA sequences.

5. The process of either of claims 1 or 2, wherein the first and second polynucleotide sequences are part of a vector capable of replicating in the host.

6. The process of claim 5, wherein the vector is a bacteriophage.

7. The process of claim 6, wherein the bacteriophage is a T-even phage.

8. The process of claim 7, wherein the bacteriophage is T2, T4 or T6.

9. The process of any of claims 1, 2, or 3, wherein the first polynucleotide sequence is part of the native genome of the host or is a heterologous nucleic acid in the native genome of said host.

10. The process of either of claims 1 or 2, wherein the second polynucleotide sequence is part of the native genome of the host or is a heterologous insertion of DNA into the native genome of said host.

11. The process of either of claims 1 or 2, wherein the second polynucleotide sequence is an insertion from the genome of Bacillus phage SPOI.

12. The process of either of claims 1 or 2, wherein the second polynucleotide sequence is an insertion from the genome of *Xanthomonas oryzae* phage X P12.

13. The process of either of claims 1 or 2 wherein said modified base is incorporated as part of a glycosylated nucleotide or a glucosylated nucleotide.

14. The process of either of claims 1 or 2, wherein the modified base which labels the first polynucleotide sequence is selected from the group consisting of a glucosylated hydroxymethyldeoxycytosine, phosphoglucuronated and glucosylated-5-(4′,5′-dihydroxypentyl) uracil, 5-hydroxymethyluracil, and 5-methycytosine.

15. The process of either of claims 1 or 2, wherein the chemically modified base which labels the first polynucleotide sequence is 5-bromo-deoxyuridine.

16. The process of any of claims 1, 2 or 3, further comprising the step of isolating from said host, a polynucleotide sequence which is part or all of the first polynucleotide sequence.

17. The process of any one of claims 1, 2 or 3, wherein said host is selected from the group consisting of bacteria, fungi, algae, plant culture cells and human culture cells.

18. The process of claim 17, wherein the said bacteria is *E. coli*.

19. The process of claim 18, wherein the *E. coli* is a mutant requiring thymine or thymidine.

20. The process of claim 16 further comprising the step of attaching a signalling moiety, a bridging moiety or at least one combination of bridging moiety and signalling moiety to the said modified base of the said first polynucleotide sequence.

21. The process of claim 20, wherein the signalling moiety, bridging moiety or combination of bridging moiety and signalling moiety are each independently covalently bound to the modified bases of the first polynucleotide sequence.

22. The process of claim 21, wherein said signalling moiety and bridging moiety are each independently selected from the group consisting of radioactive compounds, biotin, fluorescent compounds, magnetic compounds, chelating agents and other signalling and bridging moieties.

23. The process of claim 20, wherein the signalling moiety, bridging moiety or combination of bridging and signalling moiety is noncovalently bound to the modified bases of the first polynucleotide sequence.

24. The process of claim 23, wherein the signalling moiety and bridging moiety are each independently selected from the group consisting of polypeptides, lectins, antigens, antibodies, chelating agents and other signalling and bridging moieties.

25. The process of claim 24, wherein the lectin is Concanavalin A.

* * * * *